United States Patent [19]

Cremer et al.

[11] Patent Number: 5,371,227
[45] Date of Patent: Dec. 6, 1994

[54] QUINOLINE DERIVATIVES, PROCESS FOR THEIR PREPARATION, AND THEIR THERAPEUTIC APPLICATIONS

[75] Inventors: Gerard Cremer, Morangis; Pascale Goberville, Saint-Maur; Jean-Claude Muller, Morsang-sur-Orge, all of France

[73] Assignee: Synthelabo, Le Plessis Robinson, France

[21] Appl. No.: 39,828

[22] Filed: Mar. 30, 1993

Related U.S. Application Data

[63] Continuation-in-part of Ser. No. 967,120, Oct. 27, 1992, abandoned, which is a continuation-in-part of Ser. No. 792,202, Nov. 13, 1991, abandoned.

[30] Foreign Application Priority Data

Oct. 28, 1991 [FR] France ................... 91 13240

[51] Int. Cl.⁵ ........................................... C07D 401/14
[52] U.S. Cl. ........................................... 546/174; 546/176
[58] Field of Search ................... 546/174, 176

Primary Examiner—David B. Springer
Attorney, Agent, or Firm—Jacobson, Price, Holman & Stern

[57] ABSTRACT

The present invention provides a compound which is a quinoline derivative of the formula (I)

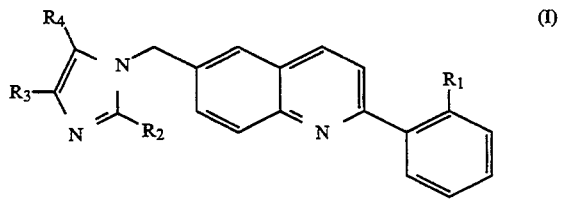

in which
$R_1$ represents either 1H-tetrazol-5-yl, or $CO_2H$,
$R_2$ represents either $(C_{1-7})$alkyl or $(C_{2-6})$alkenyl,
$R_3$ and $R_4$ represent, independently of each other, hydrogen, halogen, cyano group, $(C_{1-7})$alkyl, $(C_{3-7})$cycloalkyl$(C_{1-4})$alkyl, aryl, aryl$(C_{1-4})$alkyl, aryl$(C_{2-6})$alkenyl, $-(CH_2)_m-COR_5$ in which $m=0$ to 4 and $R_5$ represents hydrogen, $-OH$, $-(C_{1-6})$alkoxy, or $-NR_7R_8$, $R_7$ and $R_8$ representing, independently of each other, hydrogen or $-(C_{1-4})$alkyl group, or a $-(CH_2)_n-R_6$ group in which $n=1$ to 4 and $R_6$ represents $-OH$, $-(C_{1-6})$alkoxy, $-(C_{1-4})$alkoxy $-(C_{1-4})$alkoxy, or $(C_{3-7})$cycloalkyl$(C_{1-4})$alkoxy group, or a pharmaceutically acceptable salt thereof and their therapeutic applications.

12 Claims, No Drawings

QUINOLINE DERIVATIVES, PROCESS FOR THEIR PREPARATION, AND THEIR THERAPEUTIC APPLICATIONS

This application is a continuation-in-part of Ser. No. 07/967,120, filed Oct. 27, 1992, abandoned, which in turn is a continuation-in-part of Ser. No. 07/792,202, filed Nov. 13, 1991, abandoned.

The present invention relates to quinoline derivatives, their preparation and their therapeutic applications.

SUMMARY OF THE INVENTION

The compounds of the invention are of the general formula (I)

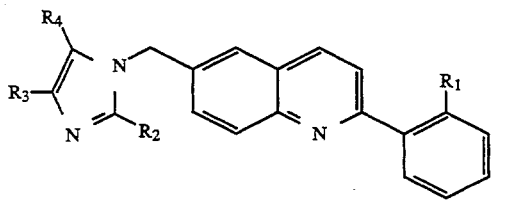

in which
$R_1$ represents either a 1H-tetrazol-5-yl group, or a $CO_2H$ group,
$R_2$ represents either a $(C_{1-7})$alkyl group or a $(C_{2-6})$alkenyl group,
$R_3$ and $R_4$ represent, independently of each other, either a hydrogen atom or a halogen atom or a cyano group or a $(C_{1-7})$alkyl group or a $(C_{3-7})$cycloalkyl$(C_{1-4})$alkyl group or an aryl group or an aryl$(C_{1-4})$alkyl group or an aryl$(C_{2-6})$alkenyl group or a $(CH_2)_m$—$COR_5$ group in which $m=0$ to 4 and $R_5$ represents a hydrogen atom, an OH group, a $(C_{1-6})$alkoxy group or an $NR_7R_8$ group, $R_7$ and $R_8$ representing, independently of each other, a hydrogen atom or a $(C_{1-4})$alkyl group or a $(CH_2)_n$—$R_6$ group in which $n=1$ to 4 and $R_6$ represents an OH group, a $(C_{1-6})$alkoxy group, a $(C_{1-4})$alkoxy$(C_{1-4})$alkoxy group or a $(C_{3-7})$cycloalkyl$(C_{1-4})$alkoxy group.

DETAILED DESCRIPTION OF THE INVENTION

The preferred compounds of the invention are those for which $R_1$ represents either a 1H-tetrazol-5-yl group or a $CO_2H$ group,
$R_2$ represents a $(C_{1-7})$alkyl group,
$R_3$ represents either a halogen atom or a $(C_{1-7})$alkyl group or an aryl$(C_{1-4})$alkyl group,
$R_4$ represents either a $(CH_2)_m$—$COR_5$ group in which $m=0$ to 4 and $R_5$ represents a hydrogen atom, an OH group, a $(C_{1-6})$alkoxy group or an $NR_7R_8$ group, $R_7$ and $R_8$ representing, independently of each other, a hydrogen atom or a $(C_{1-4})$alkyl group,
or a $(CH_2)_n$—$R_6$ group in which $n=1$ to 4 and $R_6$ represents an OH group or a $(C_{1-6})$alkoxy group.

Finally, the preferred compounds are those for which $R_1$ represents a 1H-tetrazol-5-yl group,
$R_2$ represents a butyl group,
$R_3$ represents either a chlorine atom or an ethyl group or a phenethyl group,
$R_4$ represents a $CH_2OH$, CHO, $CO_2H$, $CO_2CH_3$, $CO_2C_2H_5$ or $CH_2OCH_3$ group.

The compounds of the invention may be in free form or in the form of pharmaceutically acceptable organic or inorganic salts.

The compounds of the invention for which $R_1$ represents a 1H-tetrazol-5-yl group may be prepared according to the scheme in Appendix I.

In a first stage, 4-methylbenzenamine(para-toluidine) is reacted at the reflux temperature with a benzaldehyde of formula (II), in which X represents a bromine or iodine atom, in the presence of a catalyst such as 4-methylbenzenesulphonic acid (para-toluenesulphonic acid or PTSA), in solution in benzene. After cooling, propiolic acid is added and the mixture is heated at the reflux temperature in order to obtain a compound of formula (III).

In a second stage, a mixture of the compound (III) and of copper(I) cyanide in a solvent such as pyridine is heated in order to obtain 2-(6-methylquinolin-2-yl)benzonitrile (IV).

In a third stage, 2-(6-methylquinolin-2-yl)benzonitrile is reacted with an organometallic azide such as trimethyltin azide or a metallic azide such as sodium azide in order to obtain a compound over which a stream of gaseous hydrochloric acid is passed in order to obtain 6-methyl-2-[2-(1H-tetrazol-5-yl)phenyl]quinoline (V). The first reaction is carried out in a solvent such as xylene at the reflux temperature; the second reaction is carried out in a solvent such as toluene/tetrahydrofuran mixture at room temperature.

In a fourth stage, the tetrazole group of 6-methyl-2-[2-(1H-tetrazol-5-yl)phenyl]quinoline (V) is protected with a protecting group of formula $CR_{13}R_{14}R_{15}$, in which $R_{13}$, $R_{14}$ and $R_{15}$ each represent independently of each other a $(C_{1-2})$alkyl group or an aryl group; in this stage, the compound (V) is reacted with a protecting agent such as for example trityl chloride, at room temperature in a solvent such as dichloromethane in the presence of a base such as N-methylmorpholine or triethylamine and a compound of formula (VI) is obtained in which $R_{13}$, $R_{14}$ and $R_{15}$ are as previously defined. The protection of the tetrazole group preferably occurs in position 2.

In a fifth stage, the methyl group in position 6 of the quinoline of formula (VI) is functionalised by introducing therein a departing group. If the departing group is a bromo radical, then a compound of formula (VI) is reacted with N-bromosuccinimide in order to obtain a compound of formula (VII) in which $CR_{13}R_{14}R_{15}$ is as previously defined; the reaction is carried out at the reflux temperature in a solvent such as carbon tetrachloride in the presence of an initiator such as benzoyl peroxide or $\alpha,\alpha'$ or azobisisobutyronitrile.

In a sixth stage, a compound of formula (VII) is reacted with an imidazole of formula (VIII) in which $R_2$, $R_3$ and $R_4$ are as previously defined, in order to give a derivative of formula (IX). The reaction is carried out in a solvent such as dimethylformamide at a temperature of 0° C. to 50° C. in the presence of a base such as potassium carbonate.

In a seventh stage, deprotection of the tetrazolyl group is carried out in order to obtain a compound of formula (I a).

The compounds of the invention for which $R_1$ represents a $CO_2H$ group may be prepared according to the scheme in Appendix II.

In a first stage, 4-methylbenzenamine (paratoluidine) is reacted at the reflux temperature with a benzaldehyde of formula (II) in which X represents a bromine or an iodine atom in the presence of a catalyst such as 4-methylbenzenesulphonic acid (para-toluenesulphonic acid or PTSA) in solution in benzene. After cooling, propiolic acid is added and the mixture is heated at the reflux temperature in order to obtain the compound of formula (III).

In a second stage, a mixture of the compound (III) and copper(I) cyanide in a solvent such as pyridine is heated in order to obtain 2-(6-methylquinolin-2-yl)-benzonitrile (IV).

In a third stage, 2-(6-methylquinolin-2-yl)-benzonitrile is reacted with an alcohol R-OH (V'), where R is a branched or unbranched ($C_{1-4}$)alkyl radical, in the presence of an acid, for example sulphuric acid, in order to obtain a quinoline of formula (VI') in which R is as previously defined.

In a fourth stage, the methyl group in position 6 of the quinoline is functionalised by introducing therein a departing group. If the departing group is a bromo radical, then the quinoline of formula (VI') is reacted with N-bromosuccinimide in order to obtain the quinoline of formula (VII') in which R is as previously defined; the reaction is carried out in a solvent such as carbon tetrachloride in the presence of an initiator such as benzoyl peroxide or $\alpha,\alpha'$-azobisisobutyronitrile at the reflux temperature.

In a fifth stage, the quinoline of formula (VII') is reacted with an imidazole of formula (VIII), in which $R_2$, $R_3$ and $R_4$ are as previously defined, in order to give a derivative of formula (IX'). The reaction is carried out in dimethylformamide at a temperature of 0° C. to 50° C. in the presence of a base such as potassium hydroxide or potassium carbonate.

In a sixth stage, the ester functional group of the quinoline of formula (IX') is hydrolysed in order to obtain a compound of formula (I b).

The intermediate compounds are novel and are part of the invention. They are of the formula (X)

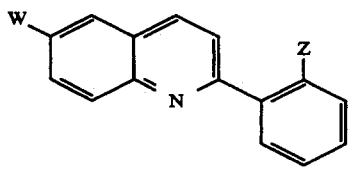

(X)

in which
W represents either a methyl group or a —$CH_2R_{11}$ group in which $R_{11}$ represents a chlorine atom, a bromine atom or a departing group $OR_{12}$, $R_{12}$ being a group such as a tosyl group or a mesyl group,
Z represents either a halogen atom or a cyano group or a 1H-tetrazol-5-yl group or a 1H-tetrazol-5-yl group protected by a protecting group of formula $CR_{13}R_{14}R_{15}$, $R_{13}$, $R_{14}$ and $R_{15}$ representing independently of each other a ($C_{1-2}$)alkyl group or an aryl group, or a COOR group, R being a branched or unbranched ($C_{1-4}$)alkyl group.

The starting compounds are commercially available or are described in the literature or can be prepared using methods which are described therein or which are known to a person skilled in the art. For example, compounds of formula (VIII) in which $R_3$ and $R_4$ are a hydrogen atom, and halogenation of these compounds, are described in EP 253310. Compounds in which $R_3$ is a hydrogen atom and $R_4$ is a —$CH_2OH$ group are prepared according to EP 253310

Compounds of formula (VIII) in which $R_3$ is an alkyl group are prepared according to Paul R., et al, J. Med. Chem., 28, 1704 (1985).

The following examples illustrate the invention.
Microanalyses and IR and NMR spectra confirm the structure of the compounds obtained.

EXAMPLE 1

2-butyl-4-chloro-1-[[2-[2-(1H-tetrazol-5-yl)phenyl]-quinolin-6-yl]methyl]1H-imidazole-5-carboxaldehyde, hydrochloride.

1.1 2-(2-bromophenyl)-6-methylquinoline 50 g (270 mmol) of 2-bromobenzaldehyde are heated to the reflux temperature, in a round-bottomed flask fitted with a Dean-Stark, with 29.5 g (276 mmol) of para-toluidine and 0.5 g of para-toluenesulphonic acid in solution in one liter benzene. When the removal of water has been completed (about 5 ml), 8.3 ml (135 mmol) of propiolic acid are added to the reaction medium previously cooled to around 50° C. A substantial release of $CO_2$ is observed and the mixture is refluxed for 3 hours. The reaction is monitored by thin-layer chromatography in a dichloromethane and hexane mixture (70/30). Under our experimental conditions, it was necessary to add a 20% excess of propiolic acid followed by refluxing for 1 hour in order to bring the reaction to completion. The solvent is evaporated under reduced pressure and the residue is purified by chromatography on a silica column, eluting with a dichloromethane and hexane mixture (70/30).

22 g of the expected derivative are recovered in the form of a crystallised compound.

wt.=22 g; m.p.=92° C.; Yield=27%; $^1$H NMR (200 MHz, CDCl$_3$): δ 2.55 (s, 3H), 7.25–7.70 (m, 7H), 8.02–8.15 (m, 2H).

Similarly, 2-(2-iodophenyl)-6-methylquinoline is prepared from 2-iodobenzaldehyde. m.p.=77°–77.5°C.

1.2 2-(6-methylquinolin-2-yl)benzonitrile

A mixture containing 15 g (50 mmol) of the compound previously obtained in 1.1 and 5 g (56 mmol) of copper(I)cyanide in 60 ml of pyridine is heated at 160°C. for 12 hours under argon. The reaction is monitored by thin-layer chromatography (TLC) in dichloromethane. The pyridine is evaporated under reduced pressure and the residue is taken up in dichloromethane. The organic phase is washed several times with an aqueous solution of ammonium hydroxide until the aqueous phase is colorless. After a last wash with water, the organic phase is dried over magnesium sulphate and the solvent is evaporated. The residue is taken up in petroleum ether.

wt.=9.6 g, m.p.=157° C., Yield=78%, 1.3 6-methyl-2-[2-(1H-tetrazol-5-yl)phenyl]quinoline hydrochloride 9.6 g (39.29 mmol) of the nitrile previously obtained in 1.2 and 14.96 g (72.7 mmol) of trimethyltin azide are introduced into 110 ml of xylene. This mixture is refluxed for 15 hours. After cooling, the solid is filtered and suspended in 115 ml of toluene and 7 ml of tetrahydrofuran. The mixture, which is cooled using an ice bath, is subjected to bubbling of hydrochloric gas for 2 hours. The insoluble fraction is recovered by filtration, then washed with toluene and with water.

wt.=13 g

1.4 6-methyl-2-[2-[2-(triphenylmethyl)-1H-tetrazol-5-yl]phenyl]quinoline 80.5 g (0.219 mol) of the compound previously obtained in 1.3, 60 ml (0.547 mol) of N-methylmorpholine and 73.1 g (0.262 mol) of trityl chloride are added to one liter of dichloromethane at room temperature. The solution is stirred overnight, taken up in water, and the organic phase is washed twice with water and then dried. The solvent is evaporated and the residue is crystallised from a minimum amount of ether.

wt.=119 g, m.p.=176°-177° C., Yield=87%.

1.5 6-bromomethyl-2-[2-[2-(triphenylmethyl)-1H-tetrazol-5-yl]phenyl]quinoline 10 g (0.189 mol) of the compound previously obtained in 1.4 is added to 300 ml of carbon tetrachloride and the mixture is heated to around 60° C. until complete dissolution has taken place. 3.7 g (0.208 mol) of N-bromosuccinimide and 60 mg (0.0037 mol) of α, α'-azobisisobutyronitrile are added all at once at this temperature. The mixture is refluxed for 2 to 3 hours until the N-bromosuccinimide disappears. 100 ml of water and 300 ml of dichloromethane are added to the cooled mixture. The organic phase is washed several times with water and then dried. The solvent is evaporated and the residue is triturated in diisopropyl ether. A 90% pure product is obtained which will be used as it is.

wt.=10.3 g 1.6 2-butyl-4-chloro-1-[[2-[2-[2-triphenylmethyl)-1H-tetrazol-5-yl]phenyl]quinolin-6-yl]methyl]-1H-imidazole-5-carboxaldehyde a) 2-butyl-5-chloroimidazole-4-methanol 9.52 g (0.071 mol) of N-chlorosuccinimide are introduced, at a temperature of between 0° and 5° C., into 10 g (0.065 mol) of 2-butylimidazole-4-methanol in suspension in 200 ml of ethyl acetate. The mixture is stirred overnight while maintaining this temperature. The solution is filtered and the solid is washed with 20 ml of ice-cold ethyl acetate, drained and washed with water in order to remove traces of succinimide and starting product, and then dried.

wt.=7.3 g, m.p.=143° C., Yield=73%.

b) 2-butyl-4-chloroimidazole-5-carboxaldehyde

A solution containing 17.3 g (0.092 mol) of the compound previously obtained, dissolved in 52 ml of acetic acid, is added dropwise, so that the temperature of the medium is kept between 22° and 28° C., to 133 g (0.243 mol) of ammonium cerium nitrate solubilised in 200 ml of water. The reaction medium is allowed to stand for 3 to 5 hours until the solution becomes colourless. The medium is cooled and the pH is adjusted to 5-6 by adding 10N sodium hydroxide. The product formed is extracted using 3 portions of ether and the organic phase is washed with sodium bicarbonate, dried and the solvent is evaporated. 16.4 g of compound are obtained which are recrystallised from cyclohexane.

wt.=13.9 g, m.p.=92°-93° C., Yield=81%.

c) 2-butyl-4-chloro-1-[[2-[2-[2-(triphenylmethyl)-1H-tetrazol-5-yl]phenyl]quinolin-6-yl]methyl]-1H-imidazole-5-carboxaldehyde 5.11 g (0.037 mol) of potassium carbonate and 19.1 g (0.028 mol), in portions, of the compound previously obtained in 1.5 are added, while cooling on an ice bath, to 5.07 g (0.027 mol) of 2-butyl-4-chloroimidazole-5-carboxaldehyde in solution in 40 ml of dimethylformamide. The mixture is stirred under argon overnight, allowing the temperature to return to room temperature. The reaction medium is poured into water, and the solid formed is recovered and dried. The compound obtained is purified by passing through a silica column, eluting with a toluene/ethyl acetate mixture (90/10).

wt.=11.9 g, m.p.=165° C., Yield=57%.

1.7 2-butyl-4-chloro-1-[[2-[2-(1H-tetrazol-5-yl)phenyl]quinolin-6-yl]methyl]-1H-imidazole-5-carboxaldehyde 10 ml (0.040 mol) of 4N hydrochloric acid are added to 11 g (0.015 mol) of the compound previously obtained in 1.6, in solution in 130 ml of tetrahydrofuran. The mixture is stirred under an argon atmosphere overnight at room temperature.

The hydrochloride salt of the expected product crystallises from the reaction medium. It is recovered by filtration and washed with 10 ml of ice-cold tetrahydrofuran.

wt.=7.4 g, m.p.=185° C. (dec), Yield=94%. $^1$H NMR (200 MHz, DMSO): δ 0.8 (t, 3H), 1.2–1.4 (m, 2H), 1.5–1.65 (m, 2H), 5.8 (s, 2H), 7.6–8.0 (m, 8H), 8.6 (d, 1H), 9.7 (s, 1H).

EXAMPLE 2

2-butyl-4-chloro-1-[[2-[2-(1H-tetrazol-5-yl)phenyl]-quinolin-6-yl]-methyl]-1H-imidazole-5-carboxylic acid 5 ml of methanol, 241 mg (3.7 mmol) of potassium cyanide, 64 μl of acetic acid and 1.5 g of manganese dioxide are added to 344 mg (0.73 mmol) of the aldehyde derivative previously obtained in 1.6. The mixture is stirred for 48 hours at room temperature. The methyl ester formed is recovered after filtration and evaporation. 2.55 ml (2.55 mmol) of 1N sodium hydroxide are immediately added and the solution is left for 3 hours at room temperature. The pH of the solution is adjusted to 3.5 and the insolubles are filtered, washed and dried.

wt.=230 mg, m.p.=170° C. (dec), Yield=70%. $^1$H NMR (200 MHz, DMSO): δ 0.8 (t, 3H), 1.2–1.4 (m, 2H), 1.5–1.65 (m, 2H), 2.65 (t, 2H), 5.8 (s, 2H), 7.45–8 (m, 8H), 8.6 (d, 1H).

EXAMPLE 3

2-butyl-4-chloro-1-[[2-[2-(1H-tetrazol-5-yl)phenyl]-quinolin-6-yl]methyl]-1H-imidazole-5-methanol

3.1 2-butyl-4-chloro-1-[[2-[2-[2-(triphenylmethyl)-1H-tetrazol-5-yl]phenyl]quinolin-6-yl]methyl]-1H-imidazole-5-methanol 330 mg (6.9 mmol) of sodium borohydride are added in small portions to 1.65 g (2.3 mmol) of the compound obtained in 1.6, in solution in 150 ml of methanol. After reacting for 30 minutes, the mixture is concentrated and poured in a 2N solution of sodium hydroxide. The compound obtained is extracted with dichloromethane. The crude product thus obtained is purified by chromatography on a silica column with a chloroform/ethyl acetate (80/20) mixture.

wt.=1.12 g, m.p.=175° C., Yield=68% 3.2 2-butyl-4-chloro-1-[[2-[2-(1H-tetrazol-5-yl)phenyl]quinolin-6-yl]methyl]-1H-imidazole-5-methanol 1.1 g of the compound obtained previously in 3.1 is dissolved in a mixture containing 31 ml of tetrahydrofuran, 31 ml of methanol and 5 ml of acetic acid. The solution is refluxed for 24 hours. The solvents are evaporated, the residue is triturated in ether and the insolubles are recovered by filtration. The product is recrystallised in 2-butanone.

wt.=450 mg, m.p.=150°-152° C., Yield=62%. $^1$H NMR (400 MHz, DMSO): δ 0.75 (t, 3H), 1.25 (m, 2H), 1.5 (m, 2H), 2.53 (m, 2H), 4.36 (s, 2H), 5.2 (s, 1H), 5.46 (s, 2H), 7.53, (m, 3H), 7.7–7.79 (m, 4H), 7.93 (d, 1H), 8.3 (d, 1H).

EXAMPLE 4

2-butyl-4-phenethyl-1-[[2-[2-(1H-tetrazol-5-yl)phenyl]quinolin-6-yl]methyl]-1H-imidazole-5-carboxaldehyde 4.1 2-butyl-4-phenylethenylimidazole-5-carboxaldehyde 10.2 g of (E)-β-tri-n-butylstannylstyrene and 1 g of tetrakis(triphenylphosphine)palladium(0) are added to 6 g of 2-n-butyl-4-iodoimidazole-5-carboxaldehyde under an argon atmosphere in 80 ml of dry toluene. The mixture is refluxed for 6 hours. The solution is clarified by filtration after adding animal charcoal and the solvent is evaporated. The residue is taken up in hexane in order to remove the tin derivatives. The compound obtained is purified in hydrochloride or oxalate form.

hydrochloride m.p.=225° C. (decomposition) oxalate m.p.=217° C. wt.=5.1 g Yield=99%.

4.2. 2-butyl-4-phenethylimidazole-5-carboxaldehyde

A solution of 2.5 g of the compound obtained previously in 4.1 and dissolved in 50 ml of ethanol is subjected to catalytic hydrogenation at room temperature and at atmospheric pressure in the presence of palladium on carbon as catalyst. After 30 minutes, the catalyst is removed by filtration and the solvent is evaporated. 2.5 g of the expected compound are obtained in the form of a gum. The compound obtained is purified in hydrochloride form.

Hydrochloride m.p.=179.5° C.

4.3 2-butyl-4-phenethyl-1-[[2-[2-[2-(triphenylmethyl)-1H-tetrazol-5-yl]phenyl]quinolin-6-yl]methyl]-1H-imidazole-5-carboxaldehyde This compound is obtained by reaction between 2-butyl-4-phenethylimidazole-5-carboxaldehyde and the bromine-containing derivative described in Example 1.5 according to the process described in Example 1.6.

m.p.=142.5° C.

4,4 2-butyl-4-phenethyl-1-[[2-[2-(1H-tetrazol-5-yl)phenyl]quinolin-6-yl]methyl]1H-imidazole-5-carboxaldehyde This compound is obtained by detritylation of the compound obtained previously in 4.3 by heating for 24 hours in methanol at the reflux temperature.

$^1$H NMR (200 MHz, CDCl$_3$): [sic] 0.8 (t, 3H), 1.25 (m, 2H), 1.6 (m, 2H), 2.5 (t, 2H), 3.1 (m, 4H), 5.75 (s, 2H), 7–7.5 (m, 11H), 7.6 (d, 1H), 7.75 (d, 1H), 7.9 (d, 1H), 9.55 (s, 1H).

EXAMPLE 5

2-butyl-4-phenethyl-1-[[2-[2-(1H-tetrazol-5-yl)phenyl]quinolin-6-yl]methyl]-1H-imidazole-5-methanol.

5.1 2-butyl-4-phenethyl-1-[[2-[2-[1-(triphenylmethyl)-1H-tetrazol-5-yl]phenyl]quinolin-6-yl]methyl]-1H-imidazole-5-methanol This compound is obtained from the compound obtained previously in 4.3, according to the process described in Example 3.1.

m.p.=150° C.

5.2 2-butyl-4-phenethyl-1-[[2-[2-(1H-tetrazol-5-yl)phenyl]quinolin-6-yl]methyl]-1H-imidazole-5-methanol This compound is obtained by detritylation of the compound obtained previously in 5.1 by heating for 24 hours in methanol at the reflux temperature.

$^1$H NMR (200 MHz, CDCl$_3$-DMSO): σ 0.8 (t, 3H), 1.3 (m, 2H), 1.6 (m, 2H), 2.65 (t, 2H), 2.9 (m, 4H), 4.15 (s, 2H), 5.4 (s, 2H), 7.15–7.9 (m, 13H), 8.1 (d, 1H).

EXAMPLE 6

6-[[2-butyl-4-chloro-5-(methoxymethyl)-1H-imidazol-1-yl]methyl]-2-[2-(1H-tetrazol-5-yl)phenyl]-quinoline 1.5 g of the compound described in Example 3 are introduced into 36 ml of methanol and 0.18 ml of concentrated sulphuric acid are added. The mixture is refluxed for 15 hours, the methanol is evaporated and the residue is taken up in a mixture of 1N sodium hydroxide and toluene. The aqueous phase is recovered and acidified to pH 3 with hydrochloric acid. The precipitate formed is filtered and it is purified by chromatography on a silica gel column, eluting with a dichloromethane/methanol/acetic acid mixture (95/5/0.1).

wt.=0.4 g, m.p.=102° C. (dec), Yield=40%.

The following table illustrates the structures and the physical properties of some compounds according to the invention.

TABLE

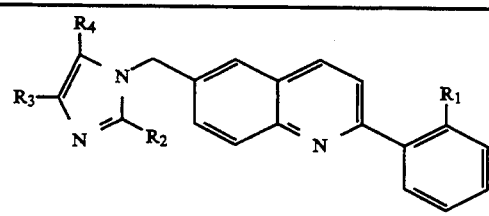

(I)

| No. | R$_1$ | R$_2$ | R$_3$ | R$_4$ | salt | m.p. (°C.) |
| --- | --- | --- | --- | --- | --- | --- |
| 1 | —CN$_4$H | —(CH$_2$)$_3$CH$_3$ | —Cl | —CHO | HCl | 185 (dec)* |
| 2 | —CN$_4$H | —(CH$_2$)$_3$CH$_3$ | —Cl | —CH$_2$OH | — | 150–152* |
| 3 | —CN$_4$H | —(CH$_2$)$_3$CH$_3$ | —Cl | —COOH | — | 170 (dec) |
| 4 | —CN$_4$H | —(CH$_2$)$_3$CH$_3$ | phenethyl | —CHO | — | —* |
| 5 | —CN$_4$H | —(CH$_2$)$_3$CH$_3$ | phenethyl | —CH$_2$OH | — | 184 (dec*) |
| 6 | —CN$_4$H | —(CH$_2$)$_3$CH$_3$ | —Cl | —CN | — | 138 (dec) |
| 7 | —CN$_4$H | —(CH$_2$)$_3$CH$_3$ | —Cl | —CH$_2$OCH$_3$ | — | 98 (dec) |
| 8 | —CN$_4$H | —(CH$_2$)$_3$CH$_3$ | —Cl | —COOCH$_3$ | — | 181–184 |
| 9 | —CN$_4$H | —(CH$_2$)$_3$CH$_3$ | —Cl | —CH$_2$OC$_2$H$_5$ | — | 170–172.5 |
| 10 | —CN$_4$H | —(CH$_2$)$_3$CH$_3$ | —Cl | —CHO | — | 138 (dec) |
| 11 | —CN$_4$H | —(CH$_2$)$_3$CH$_3$ | —Cl | —CH$_2$O(CH$_3$)$_2$ | — | 157.5–160 |
| 12 | —CN$_4$H | —(CH$_2$)$_3$CH$_3$ | —Cl | —CH$_2$O(CH$_2$)$_3$CH$_3$ | — | 91 (dec) |
| 13 | —CN$_4$H | —(CH$_2$)$_3$CH$_3$ | —Cl | —CH$_2$OCH$_2$CH(CH$_3$)$_2$ | — | 90 (dec) |
| 14 | —CN$_4$H | —(CH$_2$)$_3$CH$_3$ | —Cl | —CH$_2$OCH(CH$_3$)CH$_2$CH$_3$ | — | 98 (dec) |
| 15 | —CN$_4$H | —(CH$_2$)$_3$CH$_3$ | —Cl | —CH$_2$O(CH$_2$)$_2$OCH$_3$ | — | 119.5–122.5 |

TABLE-continued

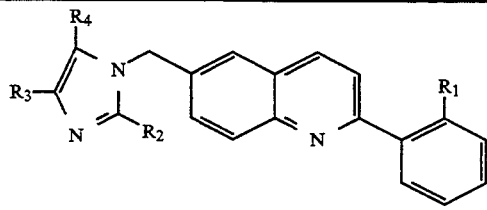

(I)

| No. | R₁ | R₂ | R₃ | R₄ | salt | m.p. (°C.) |
|---|---|---|---|---|---|---|
| 16 | —CN₄H | —(CH₂)₃CH₃ | —Cl | —CH₂O(CH₂)₂CH₃ | — | 139–140 |
| 17 | —CN₄H | —(CH₂)₃CH₃ | —Cl | —CH₂OCH₂cC₃H₇ | — | 83 (dec) |
| 18 | —CN₄H | —(CH₂)₄CH₃ | —Cl | —CHO | HCl | 188 (dec) |
| 19 | —CN₄H | —(CH₂)₄CH₃ | —Cl | —CH₂OH | — | 160–163 |
| 20 | —CN₄H | —CH₂CH₃ | —Cl | —CHO | — | 197–199 |
| 21 | —CN₄H | —(CH₂)₄CH₃ | —Cl | —COOCH₂CH₃ | — | 142–144 |
| 22 | —CN₄H | —(CH₂)₂CH₃ | —C₂H₅ | —COOCH₂CH₃ | — | 196 (dec) |
| 23 | —CN₄H | —(CH₂)₃CH₂ | —Cl | —COOCH₂CH₃ | — | 151–152 |
| 24 | —CN₄H | —CH₂CH₃ | —Cl | —COOCH₂CH₃ | — | 188–189 |
| 25 | —CN₄H | —(CH₂)₄CH₃ | —Cl | —CH₂OCH₃ | — | 106–108 |
| 26 | —CN₄H | —CH₂CH₃ | —Cl | —COOH | — | 250 |
| 27 | —CN₄H | —(CH₂)₂CH₃ | —C₂H₅ | —COOH | H₂O | 177 |
| 28 | —CN₄H | —(CH₂)₂—CH₃ | —Cl | —CHO | — | 180.5 |
| 29 | —CN₄H | —(CH₂)₂—CH₃ | —Cl | —CH₂OH | — | 166 (dec) |
| 28 | —CN₄H | —(CH₂)₂CH₃ | —Cl | —CHO | — | 180,5 |
| 29 | —CN₄H | —(CH₂)₂CH₃ | —Cl | —CH₂OH | — | 166 (dec) |
| 30 | —CN₄H | —(CH₂)₂CH₃ | —Cl | —COOCH₂CH₃ | — | 176* |
| 31 | —CN₄H | —(CH₂)₄CH₃ | —Cl | —COOH | — | 185* |
| 32 | —CN₄H | —(CH₂)₃CH₃ | —CH₂CH₃ | —COOCH₂CH₃ | — | 182* |
| 33 | —CN₄H | —(CH₂)₃CH₃ | —Cl | —COO(CH₂)₂CH₃ | — | 193* |
| 34 | —CN₄H | —(CH₂)₃CH₃ | —(CH₂)₂CH₃ | —COOH | — | 184* |
| 35 | —CN₄H | —(CH₂)₃CH₃ | —(CH₂)₃CH₃ | —COOH | — | 181* |
| 36 | —CN₄H | —(CH₂)₂CH₃ | —(CH₂)₂CH₃ | —COOH | — | 187* |
| 37 | —CN₄H | —(CH₂)₂CH₃ | —(CH₂)₃CH₃ | —COOH | — | 180* |
| 38 | —CN₄H | —(CH₂)₃CH₃ | —CH₂CH₃ | —COOH | — | 180* |
| 39 | —CN₄H | —(CH₂)₂CH₃ | —(CH₂)₂CH₃ | —COOCH₂CH₃ | — | 110* |
| 40 | —CN₄H | —(CH₂)₂CH₃ | —(CH₂)₃CH₃ | —COOCH₂CH₃ | — | 96,5* |
| 41 | —CN₄H | —(CH₂)₃CH₃ | —(CH₂)₂CH₃ | —COOCH₂CH₃ | — | 206* |
| 42 | —CN₄H | —(CH₂)₃CH₃ | —(CH₂)₃CH₃ | —COOCH₂CH₃ | — | 112* |

Legend for the table
HCl denotes hydrochloride
dec denotes decomposition
CN₄H denotes the 1H-tetrazol-5-yl group
cC₃H₇ denotes the cyclopropyl group
*a product characterised by NMR spectrum (see corresponding example)

The compounds of the invention have been the subject of pharmacological studies which have demonstrated their antagonistic properties to angiotensin II.

Test of binding of [³H]-angiotensin II to rabbit adrenal cortex 2 to 3-kg Fauves de Bourgogne male rabbits are used. After sacrificing them by cervical dislocation, the adrenal glands are excised and the cortex is dissected on a culture plate cooled using ice. It is placed in 10 ml of an ice-cold buffer solution at 10 mM of tris(hydroxymethyl)aminomethane containing 0.33M sucrose and 1 mM ethylenediaminetetraacetic acid where the pH had been adjusted to 7.4 with hydrochloric acid. The tissue is homogenised by means of an electric Potter apparatus using 13 to and fro movements of the piston at a speed of 1200 revolutions per minute. The volume of the preparation is adjusted to 25 ml with tris-sucrose buffer before centrifuging for 15 min at 1075×g. The supernatant is kept. The pellet is again homogenised after resuspending in 10 ml of tris-sucrose buffer by passing through an electric Potter and then centrifuged under the conditions previously described. The supernatant obtained is added to the first supernatant and they are centrifuged for 30 min at 47 800×g. The pellets are finally taken up in 150 volumes (that is to say 100 mg of tissue in 15 ml of buffer) in a 50 mM solution of tris-HCl buffer containing 150 mM of NaCl, 5 mM of ethylenediaminetetraacetic acid, 1.25 µg/ml of bacitracin, 100 µM of phenylmethylsulphonyl fluoride and 0.2% of bovine serum albumin (pH=7.4° at 25° C.).

This suspension contains the adrenal cortex microsomes and will be used as it is in the studies described below.

Aliquot fractions of 100 µl of suspension are incubated in the presence of [³H]-angiotensin II (New England Nuclear, with a specific activity of 61 Ci/mmol) in a final volume of 1 ml of tris-HCl buffer the composition of which has previously been described. After incubating for 30 minutes at 25° C., the microsomes are recovered by filtration on 0.45 µm Millipore HAWP ™ cellulose nitrate filters previously conditioned by soaking in a 1% solution of bovine serum albumin. The filters are washed three times with 5 ml of ice-cold tris-HCl buffer. The amount of radioactivity bound to the tissue and retained on the filters is measured by scintillation spectrometry.

The non-specific binding of [³H]-angiotensin II is measured by incubation in the presence of 1 µM of non-radioactive angiotensin II. This non-specific binding represents 5 to 10% of the total amount of radioactivity bound on the filter. The specific binding is the difference between the total radioactivity recovered on the filter and the non-specific radioactivity. The binding of [³H]-angiotensin is measured in the presence of various concentrations of the test compounds and the $IC_{50}$, the concentration of the test compound which inhibits 50% of the specific binding of $[^3H]$-angiotensin II, is graphically determined.

The $IC_{50}$ values of the compounds of the invention are between 5 nM and 10 μM.

Inhibition of the response to angiotensin II on rat blood pressure

Male rats (Sprague-Dawley, Charles River France) weighing 250 to 280 g are used, they are anaesthetized with sodium pentobarbital (55 mg/kg i.p.) and are maintained under artificial respiration (Harvard TM respirator; frequency of respiration of 70 ml per minute, volume of air 1 ml per 100 g of body weight). The animals are "spinalised" by means of a metal rod introduced through the orbit of the right eye and taken down along the length of the vertebral column. The right and left vagus nerves are sectioned (bivagotomy); the right carotid artery is ligatured, the left carotid artery being catheterised in order to measure the blood pressure using a pressure cell (Statham TM P23Db type). A femoral vein is catheterised for the purpose of administering various compounds.

The mean blood pressure variations induced by angiotensin administered intravenously at the dose of 0.5 μg/kg before administering the compounds of the invention and those induced by angiotensin administered under the same conditions 5 minutes after intravenous administration of the compounds of the invention or 30 minutes after their oral administration are measured. The compounds of the invention are administered at doses ranging from 0.01 to 100 mg/kg.

The percentage inhibition of the control response to angiotensin II is used to evaluate the antagonistic potential of the compounds of the invention to angiotensin II.

The invention includes a method of treatment of hypertensive pathologies, cardiac, renal or pulmonary insufficiencies or glaucoma which comprises administering to a patient a compound of the invention.

The compounds of the invention or their suitable salts may be used as active therapeutic substances, particularly for the treatment of various forms of hypertensive pathologies and of cardiac, renal or pulmonary insufficiencies as well as for the treatment of glaucoma.

The invention further provides a pharmaceutical composition which comprises a compound of the invention and a pharmaceutically acceptable carrier or diluent. The compounds of the invention or their suitable salts may also be used in combination with other substances possessing cardiovascular activity such as diuretics, α-blockers, β-blockers, calcium antagonists or angiotensin I converting enzyme inhibitors.

The compounds of the invention or their suitable salts may be provided in any pharmaceutical forms suitable for treatment by means of oral, parenteral, intramuscular or rectal administration: tablets, capsules, hard gelatin capsules, sterile solutions or suspensions, suppositories and the like.

For the treatment of glaucoma, the compounds of the invention, may be provided in the form of tablets, hard gelatin capsules, injectable solutions or topical eye formulations.

The compositions of the invention may be administered to patients in an amount which may range from 1 to 1000 mg per day and per patient, in one or more doses.

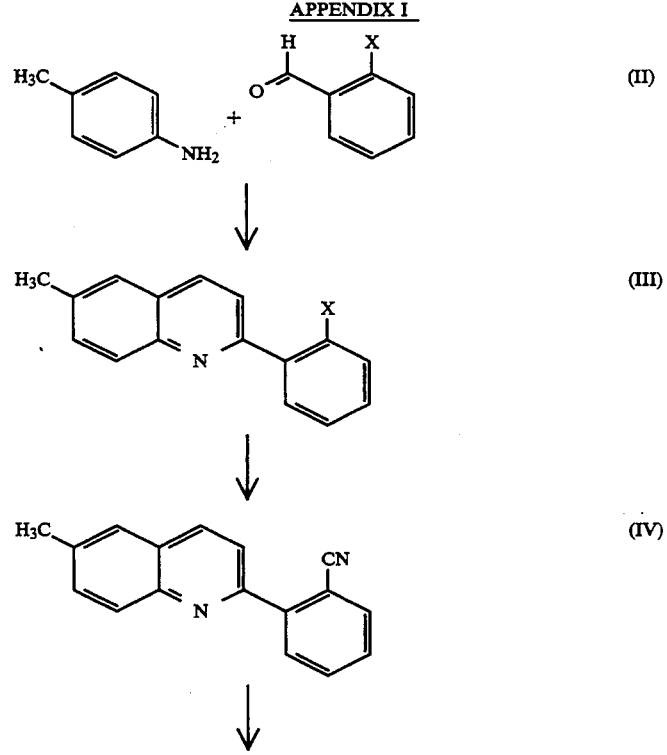

APPENDIX I
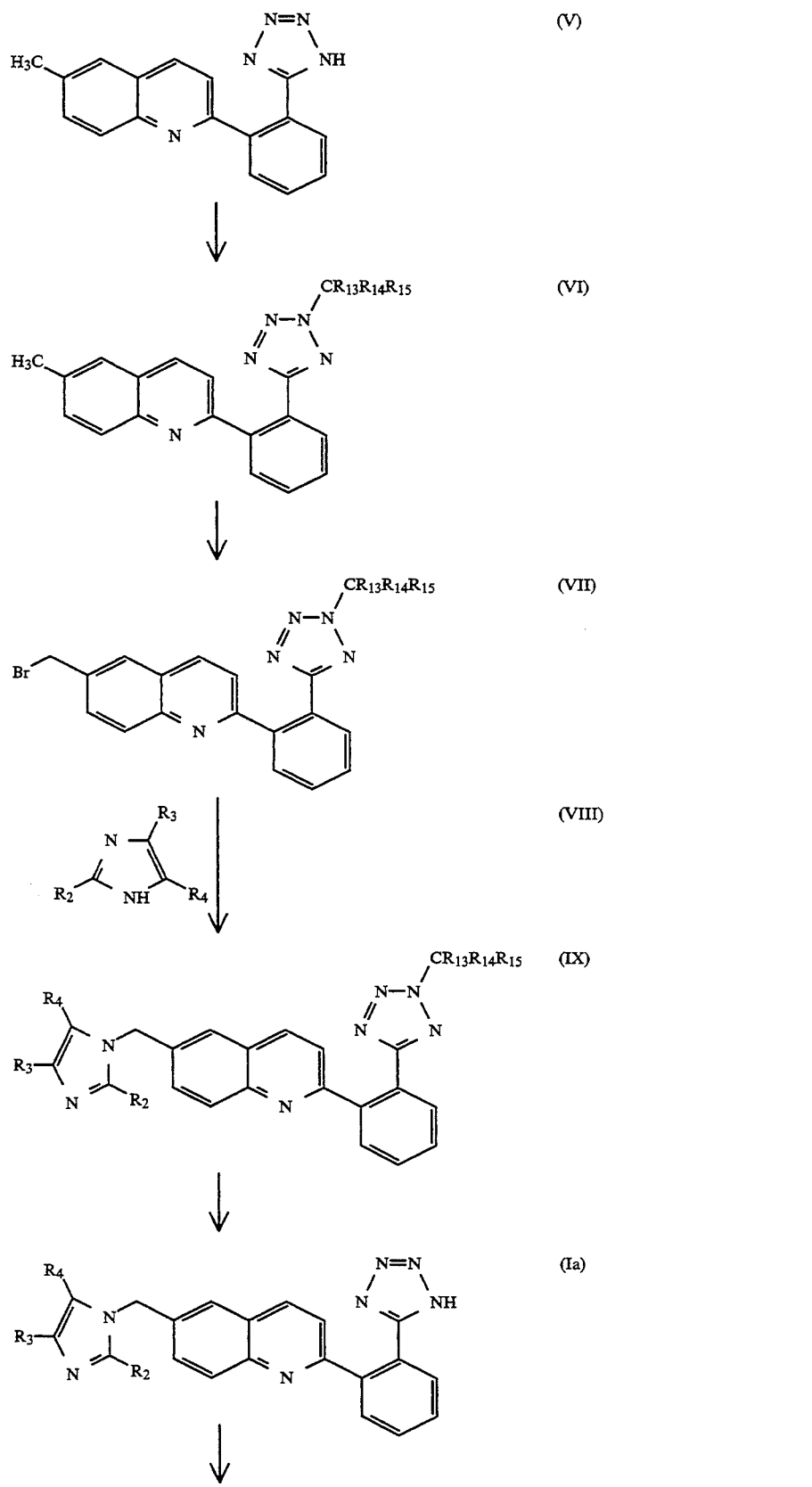

APPENDIX II
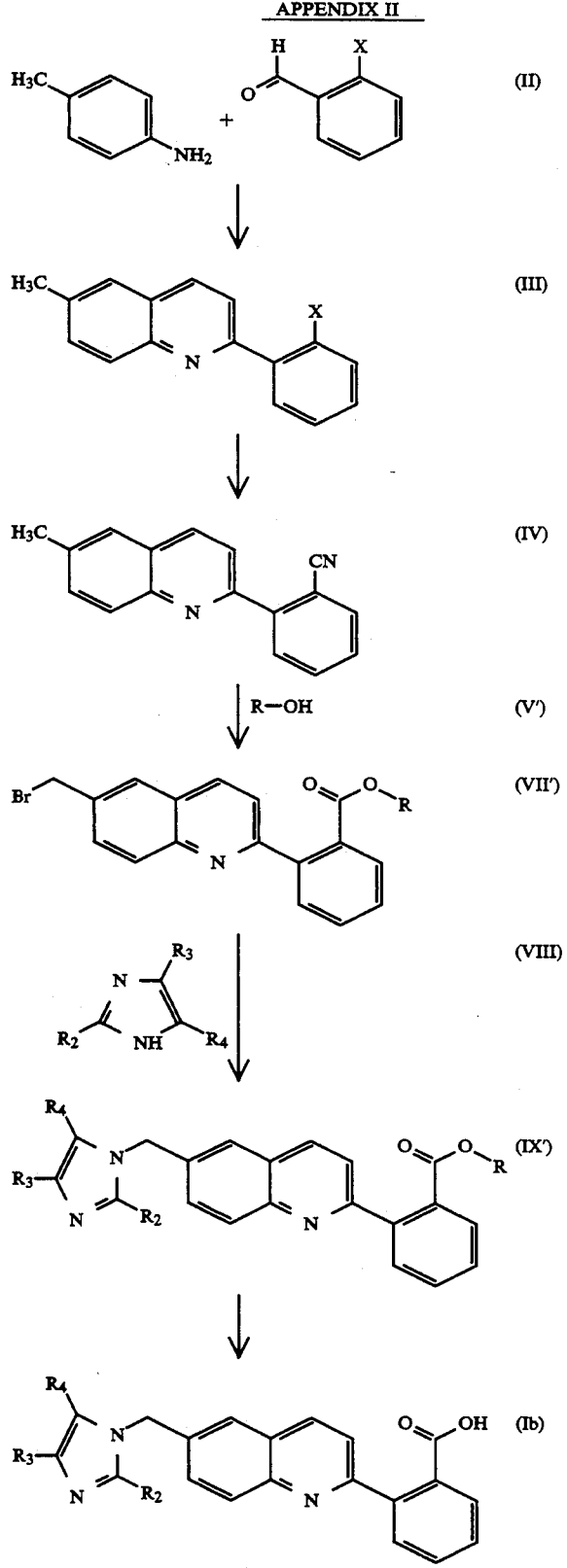
We claim:
1. A compound which is a quinoline derivative of the formula (I)

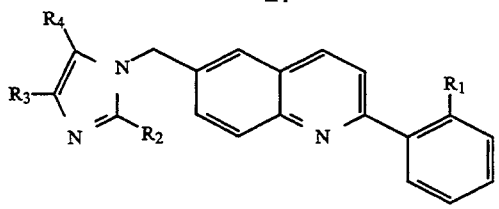

(I)

in which

R₁ represents either 1H-tetrazol-5-yl, or CO₂H,

R₂ represents either $(C_{1-7})$alkyl or $(C_{2-6})$alkenyl,

R₃ and R₄ represent, independently of each other, hydrogen, halogen, cyano group, $(C_{1-7})$alkyl, $(C_{3-7})$cycloalkyl$(C_{1-4})$alkyl, aryl, aryl$(C_{1-4})$alkyl, aryl$(C_{2-6})$alkenyl, —$(CH_2)_m$—COR₅ in which m=0 to 4 and R₅ represents hydrogen, —OH, —$(C_{1-6})$alkoxy, or —NR₇R₈, R₇ and R₈ representing, independently of each other, hydrogen or —$(C_{1-4})$alkyl group, or a —$(CH_2)_n$—R₆ group in which n=1 to 4 and R₆ represents —OH, —$(C_{1-6})$alkoxy, —$(C_{1-4})$alkoxy —$(C_{1-4})$alkoxy, or $(C_{3-7})$cycloalkyl$(C_{1-4})$alkoxy group, or a pharmaceutically acceptable salt thereof.

2. A compound according to claim 1 wherein

R₂ represents $(C_{1-7})$alkyl,

R₃ represents either halogen or $(C_{1-7})$alkyl or aryl$(C_{1-4})$alkyl, and

R₄ represents either —$(CH_2)_m$—COR₅ in which m and R₅ are as defined in claim 1, or —$(CH_2)_n$—R₆ in which n=1 to 4 and R₆ represents —OH or —$(C_{1-6})$alkoxy.

3. A compound according to claim 2 wherein R₁ represents 1H-tetrazol-5-yl,

R₂ represents butyl,

R₃ represents either chlorine or ethyl or phenethyl, and

R₄ represents CH₂OH, CHO, CO₂H, CO₂CH₃, CO₂C₂H₅ or CH₂OCH₃.

4. A compound according to claim 3 which is 2-butyl-4-chloro-1-[[2-[2-(1H-tetrazol-5-yl)phenyl]quinolin-6-yl]methyl]-1H-imidazole-5-carboxaldehyde or a pharmaceutically acceptable salt thereof.

5. A compound according to claim 3 which is 2-butyl-4-chloro-1-[[2-[2-(1H-tetrazol-5-yl)phenyl]quinolin-6-yl]methyl]-1H-imidazole-5-carboxylic acid or a pharmaceutically acceptable salt thereof.

6. A compound according to claim 3 which is 2-butyl-4-chloro-1-[[2-[2-(1H-tetrazol-5-yl)phenyl]quinolin-6-yl]methyl]-1H-imidazole-5-methanol or a pharmaceutically acceptable salt thereof.

7. A compound according to claim 3 which is 6-[[2-butyl-4-chloro-5-(methoxymethyl)-1H-imidazol-1-yl]methyl]-2-[2-(1H-tetrazol-5-yl)phenyl]quinoline or a pharmaceutically acceptable salt thereof.

8. 4-ethyl-2-propyl-1-[[2-[2-(1H-tetrazol-5-yl)phenyl]quinolin-6-yl]methyl]-1H-imidazole-5-ethylcarboxylate or a pharmaceutically acceptable salt thereof.

9. 2-butyl-4-chloro-1-[[2-[2-(1H-tetrazol-5-yl)phenyl]quinolin-6-yl]methyl]-1H-imidazole-5-ethylcarboxylate or a pharmaceutically acceptable salt thereof.

10. 4-ethyl-2-propyl-4-ethyl-1-[[2-[2-(1H-tetrazol-5-yl)phenyl]quinolin-6-yl]methyl]-H-imidazole-5-carboxylic acid or a pharmaceutically acceptable salt thereof 11. 2-butyl-4-ethyl-1-[[2-[2-(1H-tetrazol-5-yl)phenyl]quinolin-6-yl]methyl]-1H-imidazole-5-ethylcarboxylate or a pharmaceutically acceptable salt thereof 12. 2-butyl-4-ethyl-1-[[2-[2-(1H-tetrazol-5-yl)phenyl]quinolin-6-yl]methyl]-1H-imidazole-5-carboxylic acid or a pharmaceutically acceptable salt thereof

* * * * *